(12) United States Patent
Ikeda et al.

(10) Patent No.: US 8,530,203 B2
(45) Date of Patent: Sep. 10, 2013

(54) PROCESS FOR PRODUCING USEFUL SUBSTANCE

(75) Inventors: Masato Ikeda, Kamiina-gun (JP); Seiki Takeno, Kamiina-gun (JP); Yuta Mizuno, Hofu (JP); Satoshi Mitsuhashi, Tsukuba (JP)

(73) Assignees: Shinshu University, Matsumoto-shi (JP); Kyowa Hakko Bio Co., Ltd., Tokyo (JP)

( * ) Notice: Subject to any disclaimer, the term of this patent is extended or adjusted under 35 U.S.C. 154(b) by 268 days.

(21) Appl. No.: 13/061,551

(22) PCT Filed: Aug. 26, 2009

(86) PCT No.: PCT/JP2009/064821
§ 371 (c)(1), (2), (4) Date: Mar. 1, 2011

(87) PCT Pub. No.: WO2010/024267
PCT Pub. Date: Mar. 4, 2010

(65) Prior Publication Data
US 2011/0244528 A1 Oct. 6, 2011

(30) Foreign Application Priority Data

Sep. 1, 2008 (JP) ................................ 2008-223739
Feb. 24, 2009 (JP) .................................. 2009-41363

(51) Int. Cl.
*C12P 13/04* (2006.01)

(52) U.S. Cl.
USPC ....................................................... 435/106

(58) Field of Classification Search
USPC ....................................................... 435/106
See application file for complete search history.

(56) References Cited

U.S. PATENT DOCUMENTS 6,884,614 B1 * 4/2005 Pompejus et al. ......... 435/252.3
2002/0197605 A1 12/2002 Nakagawa et al.
2004/0214294 A1 10/2004 Rieping
2006/0228712 A1 10/2006 Nakagawa et al.

FOREIGN PATENT DOCUMENTS

| EP | 2287287 A1 | 2/2011 |
|---|---|---|
| JP | 2002-191370 A | 7/2002 |
| JP | 2002-338596 A | 11/2002 |
| WO | WO 96/34961 | 11/1996 |
| WO | WO 98/18937 A1 | 5/1998 |
| WO | WO 00/37497 A1 | 6/2000 |
| WO | WO 03/040292 A2 | 5/2003 |
| WO | WO 2004/033471 A2 | 4/2004 |
| WO | WO 2006/043730 A1 | 4/2006 |

OTHER PUBLICATIONS

European Patent Office, Extended European Search Report in European Patent Application No. 09809918.7 (Apr. 10, 2012).
Flores et al., *Nature Biotechnology*, 14: 620-623 (May 1996).
Kotrba et al., *Biochemical and Biophysical Research Communications*, 289, 1307-1313 (2001).
Krings et al., *Journal of Bacteriology*, 188(23): 8054-8061 (Dec. 2006).
Mizuno et al., *Nippon Nogei Kagakukai 2008 Nendo (Heisei 20 Nendo) Taikai Koen Yoshishu*, 105, Abstract 2A25a07 (Mar. 5, 2008).
Bäumchen et al., *Appl. Microbiol. Biotechnol.*, 76: 545-552 (2007).
Bäumchen, *Berichte des Forschungszentrums Jülich*, 4265: 1-91 (2007).
Bäumchen et al., *FEMS Microbiol. Lett.*, 290: 227-235 (2009).
Delaunay et al., *Enzyme and Microbial Technology*, 25: 792-768 (1999).
Ikeda et al., *Appl. Microbiol. Biotechnol.*, 62: 99-109 (2003).
Pao et al., *Microbiology and Molecular Biology Reviews*, 62(1): 1-34 (Mar. 1998).
Snoep et al., *Journal of Bacteriology*, 176(7): 2133-2135 (Apr. 1994).
European Patent Office, Communication Pursuant to Rule 114(2) EPC in European Patent Application No. 098019918.7 (Jan. 15, 2013).
Sequence alignment of RXA02447 of WO 2003/040292 A2 with SEQ ID No. 14 of European Patent Application No. 098019918.7, (Jan. 15, 2013).
Sequence alignment of conserved regions of SP family members with the corresponding region of SEQ ID No. 14 of European Patent Application No. 098019918.7 (Jan. 15, 2013).
Blast and Clustalw Search Results submitted by third-party in Japanese Patent Application No. 2010-526727 (Dec. 27, 2012).

* cited by examiner

*Primary Examiner* — Tekchand Saidha
(74) *Attorney, Agent, or Firm* — Leydig, Voit & Mayer, Ltd.

(57) ABSTRACT

The present invention provides a process for efficiently producing a useful substance; and a microorganism which belongs to coryneform bacteria and which can be used in the process. The present invention provides a process for producing a useful substance by using a microorganism belonging to coryneform bacteria, the microorganism having an ability to take a sugar, which is taken into a cell via a phosphotransferase system (PTS), into a cell via a system other than the PTS, and having an ability to produce a useful substance.

7 Claims, 1 Drawing Sheet

Fig. 1

DNA fragment for disrupting a *ptsH* gene

Fig. 2

SEQUENCE LISTING

<160> NUMBER OF SEQ ID NOS: 15

<210> SEQ ID NO 1
<211> LENGTH: 26
<212> TYPE: DNA
<213> ORGANISM: Artificial Sequence
<220> FEATURE:
<223> OTHER INFORMATION: Synthetic Primer for the ptsHup800F

<400> SEQUENCE: 1
actctgatca atcatgactg gtttgc                                        26

<210> SEQ ID NO 2
<211> LENGTH: 48
<212> TYPE: DNA
<213> ORGANISM: Artificial Sequence
<220> FEATURE:
<223> OTHER INFORMATION: Synthetic Primer for the ptsHFusR

<400> SEQUENCE: 2
agcgtcaagg tcctgtgcga taaggacggt tacagtcttg gaagccat                48

<210> SEQ ID NO 3
<211> LENGTH: 24
<212> TYPE: DNA
<213> ORGANISM: Artificial Sequence
<220> FEATURE:
<223> OTHER INFORMATION: Synthetic Primer for the ptsHdown800R

<400> SEQUENCE: 3
cagtgatcat tgggaagaat acat                                          24

<210> SEQ ID NO 4
<211> LENGTH: 48
<212> TYPE: DNA
<213> ORGANISM: Artificial Sequence
<220> FEATURE:
<223> OTHER INFORMATION: Synthetic Primer for the ptsHFusF

<400> SEQUENCE: 4
atggcttcca agactgtaac cgtccttatc gcacaggacc ttgacgct                48

<210> SEQ ID NO 5
<211> LENGTH: 28
<212> TYPE: DNA
<213> ORGANISM: Artificial Sequence
<220> FEATURE:
<223> OTHER INFORMATION: Synthetic Primer for the CGLgapAup1000F

<400> SEQUENCE: 5
aagaattggg atcccggcga aaacgaaa                                      28

<210> SEQ ID NO 6
<211> LENGTH: 51
<212> TYPE: DNA
<213> ORGANISM: Artificial Sequence
<220> FEATURE:
<223> OTHER INFORMATION: Synthetic Primer for the Cgl0181FusR

<400> SEQUENCE: 6
cggcctgaat gaaggtacta gccatgttgt gtctcctcta aagattgtag g            51

<210> SEQ ID NO 7
<211> LENGTH: 50
<212> TYPE: DNA

<213> ORGANISM: Artificial Sequence
<220> FEATURE:
<223> OTHER INFORMATION: Synthetic Primer for the Cgl3058FusR

<400> SEQUENCE: 7
tgatgtggcc ttgatgtccg tcatgttgtg tctcctctaa agattgtagg            50

<210> SEQ ID NO 8
<211> LENGTH: 51
<212> TYPE: DNA
<213> ORGANISM: Artificial Sequence
<220> FEATURE:
<223> OTHER INFORMATION: Synthetic Cgl0181FusF

<400> SEQUENCE: 8
cctacaatct ttagaggaga cacaacatgg ctagtacctt cattcaggcc g          51

<210> SEQ ID NO 9
<211> LENGTH: 26
<212> TYPE: DNA
<213> ORGANISM: Artificial Sequence
<220> FEATURE:
<223> OTHER INFORMATION: Synthetic Cgl0181RXhoI

<400> SEQUENCE: 9
gatctcgagg ctgtgatcac accatg                                     26

<210> SEQ ID NO 10
<211> LENGTH: 50
<212> TYPE: DNA
<213> ORGANISM: Artificial Sequence
<220> FEATURE:
<223> OTHER INFORMATION: Synthetic Cgl3058FusF

<400> SEQUENCE: 10
cctacaatct ttagaggaga cacaacatga cggacatcaa ggccacatca            50

<210> SEQ ID NO 11
<211> LENGTH: 26
<212> TYPE: DNA
<213> ORGANISM: Artificial Sequence
<220> FEATURE:
<223> OTHER INFORMATION: Synthetic Cgl3058RBamHI

<400> SEQUENCE: 11
gccggatcca aacatgactt tctgtg                                     26

<210> SEQ ID NO 12
<211> LENGTH: 491
<212> TYPE: PRT
<213> ORGANISM: Corynebacterium glutamicum 0181

<400> SEQUENCE: 12

Met Ala Ser Thr Phe Ile Gln Ala Asp Ser Pro Glu Lys Ser Lys
1               5                   10                  15

Leu Pro Pro Leu Thr Glu Gly Pro Tyr Arg Lys Arg Leu Phe Tyr Val
                20                  25                  30

Ala Leu Val Ala Thr Phe Gly Gly Leu Leu Phe Gly Tyr Asp Thr Gly
            35                  40                  45

Val Ile Asn Gly Ala Leu Asn Pro Met Thr Arg Glu Leu Gly Leu Thr
        50                  55                  60

Ala Phe Thr Glu Gly Val Val Thr Ser Ser Leu Leu Phe Gly Ala Ala
65                  70                  75                  80

Ala Gly Ala Met Phe Phe Gly Arg Ile Ser Asp Asn Trp Gly Arg Arg

```
                85                  90                  95
Lys Thr Ile Ile Ser Leu Ala Val Ala Phe Phe Val Gly Thr Met Ile
            100                 105                 110
Cys Val Phe Ala Pro Ser Phe Ala Val Met Val Val Gly Arg Val Leu
            115                 120                 125
Leu Gly Leu Ala Val Gly Gly Ala Ser Thr Val Val Pro Val Tyr Leu
            130                 135                 140
Ala Glu Leu Ala Pro Phe Glu Ile Arg Gly Ser Leu Ala Gly Arg Asn
145                 150                 155                 160
Glu Leu Met Ile Val Gly Gln Leu Ala Ala Phe Val Ile Asn Ala
                165                 170                 175
Ile Ile Gly Asn Val Phe Gly His His Asp Gly Val Trp Arg Tyr Met
                180                 185                 190
Leu Ala Ile Ala Ala Ile Pro Ala Ile Ala Leu Phe Phe Gly Met Leu
            195                 200                 205
Arg Val Pro Glu Ser Pro Arg Trp Leu Val Glu Arg Gly Arg Ile Asp
            210                 215                 220
Glu Ala Arg Ala Val Leu Glu Thr Ile Arg Pro Leu Glu Arg Ala His
225                 230                 235                 240
Ala Glu Val Ala Asp Val Glu His Leu Ala Arg Glu His Ala Val
                245                 250                 255
Ser Glu Lys Ser Met Gly Leu Arg Glu Ile Leu Ser Ser Lys Trp Leu
                260                 265                 270
Val Arg Ile Leu Leu Val Gly Ile Gly Leu Gly Val Ala Gln Gln Leu
            275                 280                 285
Thr Gly Ile Asn Ser Ile Met Tyr Tyr Gly Gln Val Val Leu Ile Glu
            290                 295                 300
Ala Gly Phe Ser Glu Asn Ala Ala Leu Ile Ala Asn Val Ala Pro Gly
305                 310                 315                 320
Val Ile Ala Val Val Gly Ala Phe Ile Ala Leu Trp Met Met Asp Arg
                325                 330                 335
Ile Asn Arg Arg Thr Thr Leu Ile Thr Gly Tyr Ser Leu Thr Thr Ile
                340                 345                 350
Ser His Val Leu Ile Gly Ile Ala Ser Val Ala Phe Pro Val Gly Asp
            355                 360                 365
Pro Leu Arg Pro Tyr Val Ile Leu Thr Leu Val Val Phe Val Gly
            370                 375                 380
Ser Met Gln Thr Phe Leu Asn Val Ala Thr Trp Val Met Leu Ser Glu
385                 390                 395                 400
Leu Phe Pro Leu Ala Met Arg Gly Phe Ala Ile Gly Ile Ser Val Phe
                405                 410                 415
Phe Leu Trp Ile Ala Asn Ala Phe Leu Gly Leu Phe Phe Pro Thr Ile
                420                 425                 430
Met Glu Ala Val Gly Leu Thr Gly Thr Phe Phe Met Phe Ala Gly Ile
            435                 440                 445
Gly Val Val Ala Leu Ile Phe Ile Tyr Thr Gln Val Pro Glu Thr Arg
450                 455                 460
Gly Arg Thr Leu Glu Glu Ile Asp Glu Asp Val Thr Ser Gly Val Ile
465                 470                 475                 480
Phe Asn Lys Asp Ile Arg Lys Gly Lys Val His
                485                 490
```

<210> SEQ ID NO 13
<211> LENGTH: 1476

<212> TYPE: DNA
<213> ORGANISM: Corynebacterium glutamicum 0181

<400> SEQUENCE: 13

```
atggctagta ccttcattca ggccgacagc cctgaaaaaa gtaagaagct gcccccactc      60
acagaaggtc cgtatagaaa gcggctattc tacgttgcac tagttgcgac gtttggtggg     120
ctgctcttcg gatatgacac cggagtaatc aacggtgcac tcaacccaat gacacgtgag     180
ctcggactaa ccgcgttcac cgagggtgtt gtaacttctt ccctgctgtt tggtgcagca     240
gctggtgcga tgttttttcg gtcgcatttc gacaactggg gtcgccggaa acaatcatc      300
tcacttgcag tagctttctt tgtcggcacc atgatctgcg tgtttgctcc atcttttgca     360
gtaatggttg tcggacgtgt gcttcttgga ctcgcagttg gtggcgcttc cactgttgtc     420
cctgtctacc tggctgaact tgctcctttt gaaatccgtg gctcactggc tggccgtaat     480
gagttgatga ttgttgttgg tcagctcgca gcttttgtca tcaatgcgat tattggaaat     540
gttttttggac accacgatgg tgtgtggcgc tacatgctgg caattgccgc aatcccagca     600
attgccctct tctttggaat gctccgagtt ccagaatccc acgctggct tgttgagcga      660
ggacgcattg atgaggctcg cgcagttctt gaaaccattc gccctctaga acgtgcccat     720
gcagaagttg ctgatgttga acacctagca agagaagagc acgccgtttc gagaagtcc      780
atgggcttaa gggaaatttt gtccagcaag tggcttgtgc gatcctcct ggtaggtatc      840
ggattgggtg tcgcacagca gctgaccggc atcaactcca tcatgtacta cggccaggtt     900
gttctcattg aggctggttt ctccgagaat gcagctctga tcgccaacgt ggcgccagga     960
gtgatcgcag ttgtcggtgc attcatcgca ctgtggatga tggatcgtat caaccgccgt    1020
accaccctca ttaccggtta ttctctcacc accattagcc acgtattgat cggtatcgca    1080
tccgtagcat tcccagtcgg cgatcctctt cgcccctacg ttatcttgac tctggttgtg    1140
gtcttcgtgg gatccatgca gaccttcctc aacgtagcta cctgggttat gctctctgag    1200
ctcttcccgc tggcaatgcg cggtttcgca atcggtatct cagtgttctt cctctggatc    1260
gcaaacgcgt tcctcggatt gttcttccca accatcatgg aagcagtagg actaaccgga    1320
accttcttca tgttcgccgg aatcggtgtg gttgccttga tcttcatcta cacccaggtt    1380
cctgaaactc gtggacgtac cttggaggag attgatgagg atgttacttc cggtgtcatt    1440
ttcaacaagg acatccgaaa aggaaaggtg cactaa                              1476
```

<210> SEQ ID NO 14
<211> LENGTH: 508
<212> TYPE: PRT
<213> ORGANISM: Corynebacterium glutamicum 3058

<400> SEQUENCE: 14

```
Met Thr Asp Ile Lys Ala Thr Ser Ser Thr Ser Ala Thr Thr Ala Pro
1               5                   10                  15

Thr Ala Gly Arg Pro Ala Arg Arg Leu Gly Gln Ile Ser Leu Val Ala
            20                  25                  30

Cys Leu Gly Gly Leu Leu Phe Gly Tyr Asp Thr Gly Val Ala Asn Gly
        35                  40                  45

Ala Glu Gly His Met Ala Gln Glu Leu Gly Leu Asn Val Leu Gln Leu
    50                  55                  60

Gly Val Val Ile Ser Ser Leu Val Phe Ala Ala Ala Phe Gly Ala Leu
65                  70                  75                  80

Phe Ala Gly Arg Ile Ser Asp Glu Ile Gly Arg Arg Lys Ala Ile Ile
                85                  90                  95
```

```
Thr Leu Ser Val Leu Phe Phe Leu Gly Ser Ile Leu Val Val Phe Ser
            100                 105                 110

Pro Ala Gly Glu Leu Gly Gln Phe Tyr Gly Pro Gly Phe Ala Thr Leu
            115                 120                 125

Val Thr Gly Arg Ile Met Leu Gly Leu Ala Val Gly Gly Ala Ser Thr
145         130                 135                 140

Val Val Pro Val Tyr Leu Ala Glu Leu Ala Pro Leu Glu Ile Arg Gly
145                 150                 155                 160

Ser Leu Thr Gly Arg Asn Glu Leu Ala Ile Val Thr Gly Gln Leu Leu
                165                 170                 175

Ala Phe Val Ile Asn Ala Leu Ile Ala Val Thr Leu His Gly Val Ile
                180                 185                 190

Asp Gly Ile Trp Arg Ile Met Phe Ala Val Cys Ala Leu Pro Ala Val
                195                 200                 205

Ala Leu Phe Leu Gly Met Leu Arg Met Pro Glu Ser Pro Arg Trp Leu
            210                 215                 220

Val Asn Gln Gly Arg Tyr Asp Asp Ala Arg Arg Val Met Glu Thr Val
225                 230                 235                 240

Arg Thr Pro Glu Arg Ala Lys Ala Glu Met Asp Glu Ile Ile Ala Val
                245                 250                 255

His Ser Glu Asn Asn Ala Ala Leu Pro Gly Val Lys Gln Ser Ser Gly
                260                 265                 270

Gln Ala Ser Gly Gln Val Ser Ser Lys His Thr His Met Ser Ile Gly
            275                 280                 285

Glu Val Leu Ser Asn Lys Trp Leu Val Arg Leu Leu Ile Ala Gly Ile
            290                 295                 300

Gly Val Ala Val Ala Gln Gln Leu Thr Gly Ile Asn Ala Ile Met Tyr
305                 310                 315                 320

Tyr Gly Thr Arg Val Leu Glu Glu Ser Gly Met Ser Ala Glu Met Ala
                325                 330                 335

Val Val Ala Asn Ile Ala Phe Gly Ala Val Ala Val Ile Gly Gly Leu
                340                 345                 350

Ile Ala Leu Arg Asn Met Asp Arg Leu Asp Arg Arg Thr Thr Phe Ile
            355                 360                 365

Ile Gly Leu Ser Leu Thr Thr Thr Phe His Leu Leu Ile Ala Ala Ala
            370                 375                 380

Gly Thr Leu Leu Pro Glu Gly Asn Ser Ile Arg Pro Phe Ala Ile Met
385                 390                 395                 400

Ile Leu Val Val Gly Phe Val Leu Ser Met Gln Thr Phe Leu Asn Val
                405                 410                 415

Ala Val Trp Val Trp Leu Ala Glu Ile Phe Pro Val Arg Met Lys Gly
                420                 425                 430

Ile Gly Thr Gly Ile Ser Val Phe Cys Gly Trp Gly Ile Asn Gly Val
            435                 440                 445

Leu Ala Leu Phe Phe Pro Ala Leu Val Ser Gly Val Gly Ile Thr Phe
            450                 455                 460

Ser Phe Leu Ile Phe Ala Val Val Gly Val Ile Ala Leu Ala Phe Val
465                 470                 475                 480

Thr Lys Phe Val Pro Glu Thr Arg Gly Arg Ser Leu Glu Glu Leu Asp
                485                 490                 495

His Ala Ala Phe Thr Gly Gln Ile Phe Lys Lys Ala
            500                 505
```

-continued

```
<210> SEQ ID NO 15
<211> LENGTH: 1527
<212> TYPE: DNA
<213> ORGANISM: Corynebacterium glutamicum 3058

<400> SEQUENCE: 15
atgacggaca tcaaggccac atcaagtaca tcggccacta cagcaccaac agcaggccga      60
ccagcgcgtc gacttggaca aatttccctc gtcgcctgtc tcggcggact tctcttcggc     120
tatgacaccg gtgtcgccaa cggcgccgaa ggccacatgg cacaagaact cggactcaac     180
gtgctgcagc tcggcgttgt catcagttca ctggttttcg ctgcagcctt tggcgcgctg     240
ttcgctgggc gtatctcgga cgaaatcggg cgtcgaaaag caattatcac tttgtccgtg     300
ctgttcttcc tcggatcaat cctcgtcgta ttctcccccg ccggtgagct ggggcagttc     360
tacggaccag gatttgccac cttggtcacc gggcgcatca tgttgggtct cgcggttggc     420
ggcgcctcca cagtagttcc ggtgtacctc gctgaactcg caccactaga aatccgcggc     480
tccctgaccg gccgaaacga gcttgctatc gtcaccggcc agctgcttgc cttcgtgatc     540
aacgcgctta tcgccgtcac cctacacgga gttattgatg aatctggcg catcatgttc      600 gccgtctgtg ccctccctgc cgtcgccctc ttcctcggca tgctgcggat gccggaatca     660
ccacgctggc tggtcaacca ggggcgttac gacgacgccc gccgcgtcat ggagaccgtc     720 cgtaccctg agcgtgcgaa agccgaaatg gatgaaatca tcgcggtgca ctctgaaaac      780
aatgcggcac ttcctggtgt taagcagtct tcgggccagg cttcaggcca ggtttctagc     840
aagcacaccc acatgtccat cggcgaagtc ctcagcaaca aatggctggt tcgtctgctc     900
atcgccggca tcggtgttgc agttgcccag cagctcaccg gcatcaacgc catcatgtac     960
tacggaaccc gcgtcctcga ggaatccggc atgagcgcag aaatggctgt ggttgccaac    1020
attgctttcg gtgccgttgc cgtcatcggt ggactgatcg cactgcgcaa catggaccgc    1080
ctggatcgcc gcaccacctt catcatcggc ctgtcactga ccaccaccct tcacctttg     1140 atcgcagctg ccggcactct ccttccagaa ggtaactcca ttcgaccatt cgccatcatg    1200
atccttgttg ttggggttcgt gctctccatg cagactttcc tcaacgttgc agtgtgggtg    1260
tggctggcgg aaatcttccc agtccgaatg aagggtatcg gcaccggtat ttcggtattc    1320
tgcggttggg gcatcaatgg cgtcctagcg ttgttcttcc cagcactggt ctccggcgtg    1380
ggtatcacct tctccttcct tatcttcgca gtcgtcggag tcattgccct ggcgttcgtc    1440
accaagtttg ttcctgaaac ccgtggccgc tcacttgaag aactcgatca cgcagcattc    1500
accggccaga tcttcaagaa ggcttaa                                        1527
```

PROCESS FOR PRODUCING USEFUL SUBSTANCE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 15,245 bytes ASCII (Text) file named "707770CorrectedSequenceListing.txt," created Jun. 8, 2011.

TECHNICAL FIELD

The present invention relates to a process for producing a useful substance.

BACKGROUND ART

The phosphotransferase system (hereinafter sometimes also referred to as "PTS") is a system for mediating sugar uptake and phosphorylation that is observed in many types of bacteria. Certain types of sugars are taken into cells as being phosphorylated by three components, i.e., protein EI, HPr and EII, whereby the components relay and transfer phosphoric acid derived from phosphoenolpyruvic acid to the sugars. Sugars whose cellular uptake is mediated by the PTS are called PTS sugars. It is known that when the PTS is impaired, it becomes impossible to grow on a minimal medium containing a PTS sugar as the sole carbon source (see Non-patent Literature (NPL) 1).

There are other sugars, called non-PTS sugars, which are taken into cells by a permease, not via the PTS, and then phosphorylated by a kinase. Glucose, which is generally used in fermentative production using a microorganism, is classified as a PTS sugar in many types of microorganisms. Accordingly, if a PTS-deficient microorganism belonging to the genus *Corynebacterium*, such as *Corynebacterium glutamicum*, *Escherichia coli* or the like, is used for fermentative production using glucose as a carbon source, the microorganism cannot utilize glucose, thus resulting in poor growth and low productivity.

Some *E. coli* strains have been reported to have a PTS sugar uptake system other than the PTS. For example, Non-Patent Literature 2 (NPL 2) discloses an *E. coli* strain which, as a result of a mutation of a galactose permease gene, has become able to grow in a glucose medium. However, such a system is unknown in microorganisms belonging to coryneform bacteria.

Among ORFs on the chromosomal DNA of *Corynebacterium glutamicum*, both Cgl0181 (NCgl0178) and Cgl3058 (NCgl2953) have been reported to encode proteins involved in myo-inositol transport (Non-Patent Document 3). However, it is unknown what level of glucose uptake ability is imparted to a microorganism whose expression of genes encoding these proteins has been enhanced, or what effect is given to the useful substance productivity of a microorganism by the enhanced expression of these proteins.

CITATION LIST

Non-Patent Literature

NPL 1: Biochem. Biophys. Res. Commun., 289, 1307 (2001)
NPL 2: Nat. Biotechnol., 14, 620 (1996)
NPL 3: J. Bacteriol., 188, 8054 (2006)

SUMMARY OF INVENTION

Technical Problem

An object of the present invention is to provide a process for producing a useful substance.

Solution to Problem

The present invention provides the following items (1) to (9).

(1) A process for producing a useful substance, comprising culturing a microorganism belonging to coryneform bacteria in a medium, the microorganism having an enhanced ability to take a sugar, which is taken into a cell via a phosphotransferase system (hereinafter abbreviated as "PTS"), into a cell via a system other than the PTS, and having an ability to produce a useful substance; forming and accumulating the useful substance in a culture; and collecting the useful substance from the culture.

(2) The process according to Item (1), wherein the sugar, which is taken into a cell via the PTS, is selected from the group consisting of glucose, fructose, and sucrose.

(3) The process according to Item (1) or (2), wherein the microorganism belonging to the coryneform bacteria is selected from the group consisting of the genera *Corynebacterium*, *Brevibacterium* and *Microbacterium*.

(4) The process according to any one of Items (1) to (3), wherein the microorganism belonging to the coryneform bacteria is the genus *Corynebacterium*.

(5) The process according to any one of Items (1) to (4), wherein the microorganism belonging to the coryneform bacteria is the species *Corynebacterium glutamicum*.

(6) The process according to Item (1), wherein the microorganism is *Corynebacterium glutamicum* SupH (FERN BP-10998).

(7) The process according to any one of Items (1) to (6), wherein the culturing is performed at 35° C. to 38° C.

(8) The process according to any one of Items (1) to (7), wherein the useful substance is an amino acid.

(9) The process according to Item (1), wherein the microorganism having an enhanced ability to take a sugar, which is taken into a cell via the PTS, into a cell via a system other than the PTS, and having an ability to produce a useful substance has an enhanced ability to produce a protein defined in any one of [1] to [5] below:

[1] a protein comprising the amino acid sequence shown in SEQ ID NO: 12 or 14;

[2] a protein consisting of an amino acid sequence, wherein one or more amino acid residues are added, deleted or substituted in the amino acid sequence shown in SEQ ID NO: 12 or 14, and having a myo-inositol transport activity;

[3] a protein encoded by DNA comprising the nucleotide sequence shown in SEQ ID NO: 13 or 15;

[4] a protein encoded by DNA which hybridizes with DNA comprising the nucleotide sequence complementary to the nucleotide sequence shown in SEQ ID NO: 13 or 15 under stringent conditions, and having a myo-inositol transport activity; and

[5] a protein encoded by DNA comprising a nucleotide sequence having 80% or more identity to the nucleotide sequence shown in SEQ ID NO: 13 or 15, and having a myo-inositol transport activity.

Advantageous Effects of Invention

According to the present invention, a process for efficiently producing a useful substance can be provided.

BRIEF DESCRIPTION OF DRAWINGS

In FIG. 2, black squares represent the SupH strain, and white triangles represent the ATCC31833 strain.

DESCRIPTION OF EMBODIMENTS

Any microorganism belonging to coryneform bacteria can be used as the microorganism in connection with the production method of the present invention, insofar as the microorganism has an enhanced ability to take a sugar, whose cellular uptake is generally mediated via the PTS, into a cell via a system other than the PTS, and has an ability to produce a useful substance.

Examples of coryneform bacteria include microorganisms belonging to the genera *Corynebacterium, Brevibacterium* and *Microbacterium* as defined in Bergeys Manual of Determinative Bacteriology, 8, and 599 (1974).

Specific examples of coryneform bacteria include *Corynebacterium acetoacidophilum, Corynebacterium acetoglutamicum, Corynebacterium callunae, Corynebacterium glutamicum, Corynebacterium herculis, Corynebacterium lilium, Corynebacterium melassecola, Corynebacterium thermoaminogenes, Brevibacterium saccharolyticum, Brevibacteriumim mariophilum, Brevibacterium roseum, Brevibacterium thiogenitalis, Microbacterium ammoniaphilum* and the like species.

Examples of the sugar, whose cellular uptake is generally mediated via the PTS, include glucose, fructose, sucrose and the like.

The useful substance can be any substance that can be produced by a microorganism belonging to coryneform bacteria and that is considered to be industrially useful. Examples of the useful substance include amino acids; nucleic acids; vitamins; proteins such as various enzymes; peptides such as glutathione; sugars such as xylose; sugar alcohols such as xylitol; alcohols such as ethanol; organic acids such as lactic acid and succinic acid; lipids; and the like. Amino acids, nucleic acids, and vitamins are preferable; and amino acids are particularly preferable.

Examples of amino acids include L-alanine, glycine, L-glutamine, L-glutamic acid, L-asparagine, L-aspartic acid, L-lysine, L-methionine, L-threonine, L-leucine, L-valine, L-isoleucine, L-proline, L-histidine, L-arginine, L-tyrosine, L-tryptophan, L-phenylalanine, L-serine, L-cysteine, L-3-hydroxyproline, L-4-hydroxyproline and the like. Examples of nucleic acids include inosine, guanosine, inosinic acid, guanylic acid and the like. Examples of vitamins include riboflavin, thiamine, ascorbic acid and the like.

The microorganism used in the production method of the present invention has an ability to take a sugar, whose cellular uptake is generally mediated via the PTS, into a cell via a system other than the PTS. Therefore, even when the PTS does not function, for example, when the PTS function is inhibited, the microorganism can grow on a minimal medium containing a PTS sugar as the sole carbon source, for example, on a MM agar medium (10 g of PTS sugar, 0.4 g of magnesium sulfate heptahydrate, 4 g of ammonium chloride, 2 g of urea, 3 g of potassium monohydrogen phosphate, 1 g potassium dihydrogen phosphate, 10 mg of iron sulfate heptahydrate, 1 mg of manganese sulfate pentahydrate, 5 mg of nicotinic acid, 0.1 mg of biotin, 5 mg of thiamine hydrochloride, and 20 g of Bacto Agar in 1 liter of water, and adjusted to pH 7.2) at 30 to 39° C. When the PTS of the microorganism of the present invention is no longer functioning, it is unnecessary to inhibit the PTS function.

As a method for confirming whether or not the PTS of a microorganism is functioning, a PTS sugar analogue that exhibits growth inhibition can be used. For example, the growth of a microorganism on a minimal medium containing a non-PTS sugar, such as ribose, as a carbon source and containing a PTS sugar analogue at 30° C. to 37° C. is observed. When growth inhibition is observed, it is determined that the PTS is functioning. When growth inhibition is not observed, it is determined that PTS is not functioning. The presence or absence of growth inhibition can be determined by comparing the growth of this microorganism on the minimal medium with the growth thereof on a nutrient agar medium (for example, a BY agar medium containing 7 g of meat extract, 10 g of peptone, 3 g of sodium chloride, 5 g of yeast extract, and 15 g of Bacto Agar in 1 liter of water, and adjusted to pH 7.2) at the same temperature.

An example of the PTS sugar analogue is 2-deoxyglucose, which is an analogue of glucose. The concentration of a PTS sugar analog in a minimal medium can be suitably determined using, as an index, the concentration at which a wild-type strain is inhibited from growing on the nutrient agar medium. For example, the concentration of 2-deoxyglucose is preferably 1 mg/ml.

Examples of the method of inhibiting the PTS function include a method of mutagenic treatment, and preferably methods of artificially causing a defect in the PTS using recombinant DNA techniques.

Examples of the methods using recombinant DNA techniques include a method of introducing substitution, deletion, insertion, addition, or inversion of one or more nucleotides into DNA encoding the PTS on a chromosome of coryneform bacteria or into transcriptional or translational regulatory region thereof.

The PTS is composed of three components, i.e., the proteins EI and HPr, which are commonly involved in uptake of all types of PTS sugars, and the protein EII, which is specific to each PTS sugar. Therefore, the PTS function is preferably lost by introducing substitution, deletion, insertion, addition, or inversion of one or more nucleuotides into a gene encoding the EI protein or HPr protein, both of which are common components, or into transcriptional or translational regulatory region thereof.

Examples of the method of introducing substitution, deletion, insertion, addition, or inversion of one or more nucleotides into DNA encoding the PTS or into transcriptional or translational regulatory region thereof are site-specific mutagenesis methods described in Molecular Cloning: A Laboratory Manual, 3rd Ed., Cold Spring Harbor Laboratory Press (2001); Current Protocols in Molecular Biology, John Wiley & Sons (1987-1997); Nucleic Acids Research, 10, 6487 (1982), Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985); etc.

For example, DNA from which the region that encodes a gene encoding the protein EI or HPr has been deleted is inserted into a plasmid that does not autonomously replicate in a host cell and that contains an antibiotic resistance marker gene and *Bacillus subtlis* levansucrase gene sacB [Mol.

Microbiol., 6, 1195 (1992)], and the resulting plasmid is introduced into a target microorganism. The recombinant plasmid does not autonomously replicate in the host cell. Therefore, using antibiotic tolerance present on the recombinant plasmid as an index, a selection is made to obtain a transformant in which the recombinant plasmid is incorporated in a chromosome by Campbell type homologous recombination. Subsequently, a selection is made by utilizing the fact that *Bacillus subtilis* levansucrase inserted together with the DNA from which the region that encodes the gene encoding the protein EI or HPr has been deleted produces a suicide substrate [J. Bacteriol., 174, 5462] (1992) to obtain a strain in which a host chromosomal gene encoding normal EI or HPr protein has been replaced with corresponding defective gene.

Examples of methods using recombinant DNA technology include cell fusion, transduction, etc., in addition to the above-mentioned gene replacement method.

Examples of proteins of the present invention that can enhance the ability to take a sugar, whose cellular uptake is generally mediated via the PTS, into a cell via a system other than the PTS include the following:

[1] a protein comprising the amino acid sequence shown in SEQ ID NO: 12 or 14;
[2] a protein consisting of an amino acid sequence, wherein one or more amino acid residues are added, deleted or substituted in the amino acid sequence shown in SEQ ID NO: 12 or 14, and having a myo-inositol transport activity;
[3] a protein encoded by DNA comprising the nucleotide sequence shown in SEQ ID NO: 13 or 15;
[4] a protein encoded by DNA which hybridizes with DNA comprising the nucleotide sequence complementary to the nucleotide sequence shown in SEQ ID NO: 13 or 15 under stringent conditions, and having a myo-inositol transport activity; and
[5] a protein encoded by DNA comprising a nucleotide sequence having 80% or more identity to the nucleotide sequence shown in SEQ ID NO: 13 or 15, and having a myo-inositol transport activity.

The DNAs comprising the nucleotide sequences shown in SEQ ID NO: 13 and 15 have been respectively registered as Cgl0181 (NCgl0178) and Cgl3058 (NCgl2953) in DDBJ/GenBank/EMBL. Cgl0181 (NCgl0178) and Cgl3058 (NCgl2953) encode proteins shown in SEQ ID NOS: 12 and 14, respectively, and having a myo-inositol transport activity.

The protein comprising an amino acid sequence wherein one or more amino acid residues are deleted, substituted or added and having an activity to enhance the ability to take a sugar, whose cellular uptake is generally mediated via the PTS, into a cell via a system other than the PTS can be obtained, for example, by introducing a site-directed mutation into DNA encoding a protein comprising the amino acid sequence shown in SEQ ID NO: 12 or 14 (for example, DNA comprising the nucleotide sequence shown in SEQ ID NO: 13 or 15) by site-directed mutagenesis described in Molecular Cloning: A Laboratory Manual, Second Edition, Cold Spring Harbor Laboratory Press (1989) (hereinafter simply referred to as "Molecular Cloning, Second Edition"); Current Protocols in Molecular Biology, John Wiley & Sons (1987-1997) (hereinafter simply referred to as "Current Protocols in Molecular Biology"); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985); etc.

The number of amino acids that are deleted, substituted or added is not particularly limited, and is generally within the range in which deletion, substitution or addition can be done by a known method, such as the above site-directed mutagenesis. The number of amino acids is typically 1 to several tens, preferably 1 to 20, more preferably 1 to 10, and still more preferably 1 to 5.

The expression "an amino acid sequence, wherein one or more amino acid residues are added, deleted or substituted in the amino acid sequence shown in SEQ ID NO: 12 or 14" means that the amino acid sequence can include the deletion, substitution or addition of one or a plurality of amino acids at any position in the same sequence.

The position of an amino acid at which one or more amino acids can be deleted or added can be, for example, 1 to several amino acids from the N or C terminus of the amino acid sequence shown in SEQ ID NO: 12 or 14.

Deletion, substitution and addition can be simultaneously included in one sequence, and amino acids to be substituted or added can be natural or non-natural. Examples of the natural amino acids include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine and the like.

Examples of the mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine.

Group B: aspartic acid, glutamic acid, isoaspartic acid, isoglutamic acid, 2-aminoadipic acid, 2-aminosuberic acid.

Group C: asparagine, glutamine.

Group D: lysine, arginine, ornithine, 4-diaminobutanoic acid, 2,3-diaminopropionic acid.

Group E: proline, 3-hydroxyproline, 4-hydroxyproline.

Group F: serine, threonine, homoserine.

Group G: phenylalanine, tyrosine.

To possess an activity to enhance the ability to take a sugar, whose cellular uptake is generally mediated via the PTS, into a cell via a system other than the PTS, the protein of the present invention preferably has 80% or more, more preferably 90% or more, still more preferably 98% or more, and particularly preferably 99% or more homology or identity to the amino acid sequence shown in SEQ ID NO: 12 or 14.

The homology or identity among amino acid sequences or nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. Programs called BLASTN and BLASTX have been developed based on the algorithm BLAST (J. Mol. Biol. 215: 403 (1990)). For BLASTN analysis of a nucleotide sequence based on BLAST, the parameters are set, for example, to score=100, and wordlength=12. For BLASTX analysis of an amino acid sequence based on BLAST, the parameters are set, for example, to score=50, and wordlength=3. To obtain gapped alignments, Gapped BLAST can be utilized as described in Altschul et al. (1997, Nucleic Acids Res. 25: 3389-3402). Alternatively, PSI-Blast or PHI-Blast can be used to perform an iterated search that detects distant relationships between molecules (Id.) and relationships between molecules that share a common pattern. When utilizing BLAST, Gapped BLAST, PSI-Blast and PHI-Blast programs, the default parameters of the respective programs can be used. See http://www.ncbi.nlm.nih.gov.

Proteins comprising an amino acid sequence having 80% or more, preferably 90% or more, more preferably 95% or more, still more preferably 98% or more, and particularly preferably 99% or more homology or identity to the amino acid sequence shown in SEQ ID NO: 12 or 14, the protein capable of enhancing the ability to take a sugar, whose cellular uptake is generally mediated via the PTS, into a cell via a system other than the PTS in coryneform bacteria having an ability to produce a useful substance are also proteins of the present invention.

In this specification, "hybridize" means that a DNA hybridizes under specific conditions with another DNA having a specific nucleotide sequence, or a portion of the DNA. Thus, the nucleotide sequence of the DNA having a specific nucleotide sequence or portion of the DNA can have a length such that the DNA or portion thereof can be used as a probe in Northern or Southern blot analysis, or as oligonucleotide primers in PCR analysis. Examples of the DNA used as a probe include DNAs that are at least 100 nucleotides, preferably 200 nucleotides or more, and more preferably 500 nucleotides or more in length. DNAs of at least 10 nucleotides, and preferably 15 nucleotides or more in length can also be used.

Methods for DNA hybridization experiments are well known. Such experiments can be conducted by determining hybridization conditions, for example, according to the disclosure in Molecular Cloning, Second Edition, Third Edition (2001); Methods for General and Molecular Bacteriology, ASM Press (1994); Immunology Methods Manual, Academic Press (Molecular); and many other standard textbooks.

Hybridization under stringent conditions as mentioned above can be carried out, for example, in the following manner. A filter with DNA immobilized thereon and a probe DNA are incubated in a solution containing 50% formamide, 5×SSC (750 mM sodium chloride and 75 mM sodium citrate), 50 mM sodium phosphate (pH 7.6), 5× Denhardt's solution, 10% dextran sulfate, and 20 µg/l denatured salmon sperm DNA at 42° C. overnight, followed by washing the filter in 0.2×SSC solution of about 65° C. Less stringent conditions can also be employed. The stringent conditions can be modified by adjusting the concentration of formamide (the conditions become less stringent as the concentration of formamide is lowered) and by changing the salt concentration and the temperature conditions. Hybridization under less stringent conditions can be carried out, for example, by incubating a filter with DNA immobilized thereon and a probe DNA in a solution containing 6×SSCE (20×SSCE: 3 mol/l sodium chloride, 0.2 mol/l sodium dihydrogenphosphate, and 0.02 mol/l EDTA, pH 7.4), 0.5% SDS, 30% formamide and 100 µg/l denatured salmon sperm DNA at 37° C. overnight, and washing the filter with 1×SSC solution containing 0.1% SDS of 50° C. Hybridization under still less stringent conditions can be carried out, for example, by performing hybridization using a solution having a high salt concentration (for example, 5×SSC) under the above-mentioned less stringent conditions, followed by washing.

The various conditions described above can also be set by adding or changing a blocking reagent to suppress the background in hybridization experiments. The addition of a blocking reagent as described above can also be accompanied by the alteration of hybridization conditions to make the conditions suitable for the purpose.

Examples of the DNA that hybridizes under stringent conditions includes DNA having at least 80% homology, preferably 90% or more homology, more preferably 95% or more homology, still more preferably 98% or more homology, and particularly preferably 99% or more homology to the nucleotide sequence shown in SEQ ID NO: 13 or 15 as calculated by the use of program such as BLAST or FASTA described above based on the above parameters.

Whether a DNA that hybridizes with the above-mentioned DNA under stringent conditions, or a DNA that encodes a protein consisting of an amino acid sequence wherein one or more amino acids are added, deleted or substituted, and having a myo-inositol transport activity, encodes a protein that enhances the ability of coryneform bacteria to take a sugar, whose cellular uptake is generally mediated via the PTS, into a cell via a system other than the PTS can be confirmed by checking whether coryneform bacteria having the DNA can grow in a medium containing a sugar that cannot be taken into a cell via the PTS, as the sole carbon source.

The DNA encoding a protein that enhances the ability to take a sugar, whose cellular uptake is generally mediated via the PTS, into a cell via a system other than the PTS can be obtained from a microorganism belonging to coryneform bacteria by PCR using chromosomal DNA prepared by the method of Saito et al. [Biochim. Biophys. Acta, 72, 619 (1963)] as a template and using primer DNAs designed and synthesized based on the nucleotide sequence shown in SEQ ID NO: 13 or 15.

The DNA of the present invention can be obtained, for example, by PCR using chromosomal DNA prepared from *Corynebacterium glutamicum* ATCC13032 or ATCC31833 as a template and using DNAs having 5'-terminal and 3'-terminal regions of the nucleotide sequence shown in SEQ ID NO: 2 or 4 as a primer set.

Specific examples of the DNA of the present invention that can be obtained include Cgl0181 (NCgl0178) comprising the nucleotide sequence shown in SEQ ID NO: 13, and Cgl3058 (NCgl2953) comprising the nucleotide sequence shown in SEQ ID NO: 15.

The DNA of the present invention can also be obtained by a hybridization method using partial or full length DNA comprising the nucleotide sequence shown in SEQ ID NO: 13 or 15 as a probe or by chemical synthesis of the DNA comprising the nucleotide sequence shown in SEQ ID NO: 13 or 15 by a known method, based on the nucleotide sequence shown in SEQ ID NO: 13 or SEQ ID NO: 15.

The DNA of the present invention or DNA used in the production method of the present invention can also be obtained by conducting a search, through various gene sequence databases, for a sequence having at least 80% or at least 90% homology, preferably 95% or more homology, more preferably 98% or more homology, particularly preferably 99% or more homology to a nucleotide sequence of DNA encoding the amino acid sequence shown in SEQ ID NO: 12 or 14, and obtaining the desired DNA, based on the nucleotide sequence obtained by the search, from a chromosomal DNA or cDNA library of an organism having the nucleotide sequence according to the above-described method.

The nucleotide sequence of the DNA can be determined by a conventional sequencing method, such as the dideoxy method [Proc. Natl. Acad. Sci., USA, 74, 5463 (1977)], or by using a nucleotide sequencer, such as the 373A DNA Sequencer (a product of Perkin-Elmer Corp.).

In cases where the obtained DNA is found to be a partial DNA by the nucleotide sequence analysis, the full length DNA can be obtained by Southern hybridization of a chromosomal DNA library using the partial DNA as a probe.

The obtained DNA can be used as-is. If necessary, the DNA can be modified by substituting one or more nucleotides to obtain the codon that is most suitable for the expression of coryneform bacteria. Further, if necessary, a DNA fragment having a suitable length and containing a region that encodes the protein of the present invention can be prepared. The DNA or DNA fragment is ligated downstream of a promoter of an expression vector suitable for the expression of coryneform bacteria to produce a recombinant DNA.

The vectors that can be preferably used are those capable of autonomous replication or integration into the chromosome in coryneform bacteria and containing a promoter at a position appropriate for the transcription of the DNA of the present invention.

Examples of preferable vectors include pCG1 (Japanese Unexamined Patent Publication No. 57-134500); pCG2 (Japanese Unexamined Patent Publication No. 58-35197); pCG4 (Japanese Unexamined Patent Publication No. 57-183799); pCG11 (Japanese Unexamined Patent Publication No. 57-134500); pCG116, pCE54, and pCB101 (all disclosed in Japanese Unexamined Patent Publication No. 58-105999); pCE51, pCE52, and pCE53 [all described in Molecular and General Genetics, 196, and 175 (1984)]; and the like.

The recombinant DNA produced by inserting the DNA of the present invention into such a vector preferably comprises a promoter, a ribosome binding sequence, the DNA of the present invention, and a transcription termination sequence. A gene which controls a promoter can also be contained in the recombinant DNA.

Any promoter that functions in host cells (coryneform bacteria) can be used. Examples of promoters include promoters derived from *E. coli* and phages, such as a trp promoter ($P_{trp}$), a lac promoter, a $P_L$ promoter, a $P_R$ promoter, and a T7 promoter. Artificially designed or modified promoters can be also used, and examples thereof include a promoter wherein two Ptrp are tandemly arranged ($P_{trp \times 2}$); a tac promoter; a T7-lac promoter; a let I promoter; and a P54-6 promoter for expression in microorganisms belonging to the genus *Corynebacterium* [Appl. Microbiol. Biotechnol., 53, 674-679 (2000)].

It is preferable that the distance between the Shine-Dalgarno sequence, which is a ribosome-binding sequence, and the initiation codon has been adjusted appropriately (for example, 6 to 18 nucleotides). Although a transcription termination sequence is not always necessary, it is preferable to place a transcription termination sequence immediately downstream of the structural gene.

The obtained recombinant DNA is introduced into the coryneform bacteria that are used as a host.

As a method for introducing the recombinant DNA, any method capable of introducing DNA into coryneform bacteria can be used. Examples of the usable methods include a method using calcium ions [Proc. Natl. Acad. Sci., USA, 69, 2110 (1972)], a protoplast method (Japanese Unexamined Patent Publication No. 1988-248394), an electroporation method [Nucleic Acids, Res., 16, 6127 (1988)], and the like.

The DNA encoding a protein having an activity to enhance the ability to take a sugar, which is generally mediated via the PTS, into a cell via a system other than the PTS can be integrated into a chromosome of coryneform bacteria, or can be introduced as a plasmid into coryneform bacteria to form a transformant. The DNA that encodes a protein having an activity to enhance the ability to take a sugar, which is generally mediated via the PTS, into a cell via a system other than the PTS is preferably derived from coryneform bacteria.

The microorganism of the present invention can be obtained, for example, by subjecting a microorganism belonging to coryneform bacteria to mutagenesis by using a mutagenizing agent such as N-methyl-N'-nitro-N-nitroso guanidine [Microorganism Experiment Manual (Biseibutsu Jikken Manual), 1986, page 131, Kodansha Scientific Ltd.] or by UV light irradiation to obtain mutant strains, and selecting therefrom a strain having an ability to take a sugar, whose cellular uptake is generally mediated via the PTS, into a cell via a system other than the PTS.

For example, after the PTS function of the strains obtained by mutagenesis is inhibited according to the above method, a strain that can grow on a minimal medium containing a PTS sugar as the sole carbon source at 30 to 39° C., preferably 35 to 39° C., and more preferably 37 to 39° C., is selected.

The strain that can take a PTS sugar into a cell via a non-PTS system can also be obtained at a frequency of $10^{-5}$ to $10^{-6}$ by spontaneous mutation, from the PTS-deficient strains of a microorganism belonging to coryneform bacteria, which are prepared beforehand by the above method.

The phrase "having an ability to produce a useful substance" means that the microorganism can produce one or more types of useful substances. During the breeding of the microorganism, if necessary, the ability to produce a desired useful substance can be artificially imparted or enhanced by a known method.

Examples of known methods thereof include the following:

(a) a method of reducing or removing at least one mechanism of controlling the biosynthesis of a useful substance;

(b) a method of enhancing the expression of at least one enzyme involved in the biosynthesis of a useful substance;

(c) a method of increasing the copy number of at least one enzyme gene involved in the biosynthesis of a useful substance;

(d) a method of attenuating or blocking at least one metabolic pathway to produce metabolites other than a useful substance, which branches off from a biosynthetic pathway of a useful substance; and (e) a method of selecting a cell strain that is highly resistant to an analogue of a useful substance, as compared with a wild-type strain.

The above known methods can be used alone or in a combination of two or more.

Specific examples of the above methods (a) to (e), for example, to produce an amino acid as a useful substance are described in the following publications. Method (a) is described in Agric. Biol. Chem., 43, 105-111 (1979); J. Bacteriol., 110, 761-763 (1972); Appl. Microbiol. Biotechnol., 39, 318-323 (1993); and the like. Method (b) is described in Agric. Biol. Chem., 43, 105-111 (1979); J. Bacteriol., 110, 761-763 (1972); and the like. Method (c) is described in Appl. Microbiol. Biotechnol., 39, 318-323 (1993); Agric. Biol. Chem., 39, 371-377 (1987); and the like. Method (d) is described in Appl. Environ. Microbiol., 38, 181-190 (1979); Agric. Biol. Chem., 42, 1773-1778 (1978); and the like. Method (e) is described in Agric. Biol. Chem., 36, 1675-1684 (1972); Agric. Biol. Chem., 41, 109-116 (1977); Agric. Biol. Chem., 37, 2013-2023 (1973); Agric. Biol. Chem., 51, 2089-2094 (1987); and the like. With reference to these publications, microorganisms capable of forming and accumulating various amino acids can be produced.

Further, many methods for producing a microorganism capable of forming and accumulating an amino acid according to any one of, or a combination of, the above methods (a) to (e) are described in Biotechnology 2nd ed., vol. 6, Products of Primary Metabolism (VCH Verlagsgesellschaft mbH, Weinheim, 1996), section 14a or 14b; Advances in Biochemical Engineering/Biotechnology 79, 1-35 (2003); and Amino san Hakko (Amino acid fermentation), Japan Scientific Societies Press, Hiroshi Aida et al. (1986). Specific methods for producing a microorganism capable of forming and accumulating an amino acid are also described in many reports other than the above-mentioned publications, such as Japanese Unexamined Patent Publication No. 2003-164297; Agric.

Biol. Chem., 39, 153-160 (1975); Agric. Biol. Chem., 39, 1149-1153 (1975); Japanese Unexamined Patent Publication No. 1983-13599; J. Gen. Appl. Microbiol., 4, 272-283, (1958); Japanese Unexamined Patent Publication No. 1988-94985; Agric. Biol. Chem., 37, 2013-2023 (1973); WO 97/15673; Japanese Unexamined Patent Publication No. 1981-18596; Japanese Unexamined Patent Publication No. 1981-144092; and Japanese Unexamined Patent. Publication No. 2003-511086. With reference to these publications, a microorganism having an ability to produce one or more kinds of amino acids can be produced.

There are also many reports on methods for imparting to a microorganism the ability to produce a useful substance other than amino acids. Any known method can be used to prepare the microorganism to be used in the production method of the present invention.

Production of a useful substance using a microorganism having an enhanced ability to take a sugar, whose cellular uptake is generally mediated via the PTS, into a cell via a system other than the PTS can be carried out according to a usual method for producing a useful substance using a microorganism.

For example, a useful substance can be efficiently produced by culturing a microorganism in a medium, and collecting the useful substance produced and accumulated in the culture.

Any natural or synthetic medium can be used, insofar as the medium contains a carbon source, a nitrogen source, inorganic salts, etc., in appropriate amounts.

Any substance that can be assimilated by the microorganism can be used as a carbon source. However, a PTS sugar that has become capable of being taken into a cell via a non-PTS system is preferably used.

Examples of nitrogen sources include various inorganic and organic ammonium salts, such as ammonia, ammonium chloride, ammonium sulfate, ammonium carbonate, and ammonium acetate; urea and other nitrogen-containing compounds; nitrogen-containing organic substances such as meat extract, yeast extract, corn steep liquor, and soybean hydrolysate; and the like.

Examples of inorganic salts include dipotassium hydrogen phosphate, potassium dihydrogen phosphate, ammonium sulfate, sodium chloride, magnesium sulfate, calcium carbonate, and the like.

If necessary, trace nutrient sources such as biotin, thiamine, nicotinamide, and nicotinic acid can also be added. Such trace nutrient sources can be substituted with a meat extract, yeast extract, corn steep liquor, casamino acid, and the like.

Culturing is performed under aerobic conditions by a shaking culture, deep aeration agitation culture, or the like. In general, the culture temperature is preferably from 20° C. to 42° C., and more preferably from 30° C. to 39° C. The pH of the medium is preferably maintained near neutral in the range of pH 5 to pH 9. The pH of the medium is adjusted by using an inorganic or organic acid, alkaline solution, urea, calcium carbonate, ammonia, etc.

The culturing period generally ranges from 1 to 6 days, and a desired useful substance such as L-amino acid can be produced and accumulated in the culture. After culturing, precipitates such as cells are removed from the culture, and the target useful substance can be collected from the culture by using a combination of known methods, such as activated carbon treatment and ion exchange resin treatment.

The microorganism of the present invention can grow well even at high temperatures, for example, 37° C. to 39° C., at which the growth rate of usual coryneform bacteria is lowered. Therefore, culturing to produce a useful substance can be performed at high temperatures, thereby reducing cooling costs during the summer season and also lowering the risk of bacterial contamination.

The examples below serve to illustrate the present invention, but should not be construed as limitations on the scope of the invention.

EXAMPLE 1

(1) Construction of a DNA Fragment for Disrupting ptsH Gene

Based on genomic information on the *Corynebacterium glutamicum* wild-type strain ATCC13032 obtained from DNA Data Bank of Japan (DDBJ) (http://gib.genes.nig.ac.jp/single/index.php?spid=CgluATCC13032), two primers (ptsHup800F; SEQ ID NO: 1, and ptsHFusR; SEQ ID NO: 2) for amplifying the upstream region of ptsH [Gene Number: Cgl1937 (NCgl1862)], and two primers for amplifying the downstream region of ptsH (ptsHdown800R; SEQ ID NO: 3 and ptsHFusF; SEQ ID NO: 4) were designed.

Figure 1:
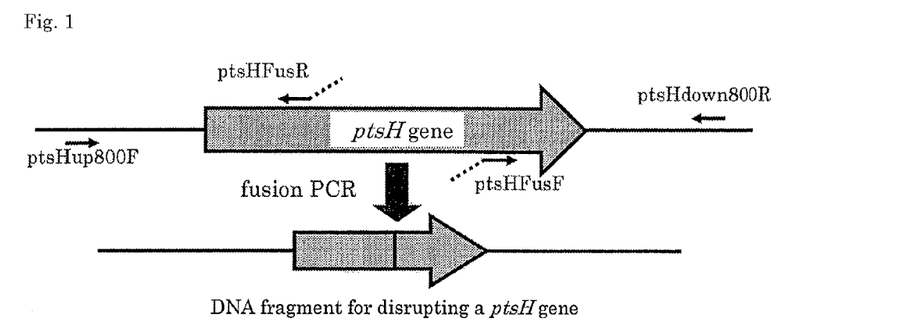
FIG. 1 is a schematic diagram depicting the construction of a DNA fragment for disrupting ptsH gene, and indicating the approximate positions to which primers bind.

To perform second PCR (fusion PCR) for ligating the upstream and downstream fragments amplified by the first PCR, DNA comprising the nucleotide sequence complementary to about 25 nucleotide sequence at 3' end of the 5'-primer (ptsHFusF; SEQ ID NO: 4) for downstream amplification was added to 5' end of the 3'-primer (ptsHFusR; SEQ ID NO: 2) for upstream amplification, and DNA comprising the nucleotide sequence complementary to about 25 nucleotide sequence at 3' end of the ptsHFusR was added to 5' end of the ptsHFusF. Further, restriction enzyme FbaI site, and nucleotide used as scaffold for the enzyme were added to 5' end of the 5'-primer (ptsHup800F) for upstream amplification and to 5' end of the 3'-primer (ptsHdown800R) for downstream amplification. FIG. 1 is a schematic diagram depicting the construction of a DNA fragment for disrupting ptsH gene, and indicating the approximate positions to which the primers bind. SEQ ID NO: 1 to 4 show the nucleotide sequences of above 4 types of primers, ptsHup800F, ptsHFusR, ptsHdown800R and ptsHFusF, respectively.

A chromosomal DNA of the *Corynebacterium glutamicum* ATCC31833 strain, which is a wild-type strain of *Corynebacterium glutamicum* (hereinafter referred to as "ATCC 31833 strain"), was prepared according to the method of Saito et al. [Biochim. Biophys. Acta 72, 619 (1963)].

Using this chromosomal DNA as a template, first PCR for amplifying the upstream and the downstream regions of the ptsH gene was performed. As a result, the DNA fragment about 0.83 kb upstream and the DNA fragment about 0.82 kb downstream were obtained. Subsequently, second PCR for ligating the upstream and the downstream fragments was performed to obtain the DNA fragment about 1.65 kb as the DNA fragment for disrupting the ptsH gene (FIG. 1).

(2) Construction of a Plasmid for Disrupting ptsH Gene

The plasmid pESB30 wherein 2.6 kb PstI DNA fragment [Mol. Microbiol., 6, 1195 (1992)] containing *Bacillus subtilis* Levansucrase gene sacB was ligated to PstI cleavage site of *Escherichia coli* vector pHSG299 [Gene, 61, 63, (1987)] carrying kanamycin resistant gene was prepared. The plasmid and the above-obtained DNA fragment for disrupting ptsH gene were cleaved with restriction enzymes, FbaI and BamHI, respectively. Using the reaction products, *Escherichia coli* DH5a (Toyobo Co., Ltd.) was transformed according to a usual method [Molecular Cloning: A Laboratory Manual, 3rd Ed., 2001, Cold Spring Harbor Laboratory Press].

The transformants were cultured on LB agar medium (10 g of Bacto Tryptone (Difco Laboratories), 5 g of yeast extract (Difco Laboratories), 10 g of sodium chloride, 16 g of Bacto Agar (Difco) in 1 L of water, and adjusted to pH 7.0) containing 20 µg/ml of kanamycin to select a transformant.

The transformant was inoculated and cultured overnight in LB medium (same composition as the LB agar medium except for not containing agar) containing 20 µg/ml kanamycin, and the plasmid was prepared from the culture by the alkali SDS method [Molecular Cloning: A Laboratory Manual, 3rd Ed., 2001, Cold Spring Harbor Laboratory Press]. By the nucleotide sequence analysis, it was confirmed that the plasmid has structure such that an approximate 1.65 kb DNA fragment for disrupting the ptsH gene was inserted into pESB30. This plasmid was designated pCΔptsH.

(3) Construction of a *Corynebacterium glutamicum* ptsH-Disrupted Strain

The plasmid pCΔptsH was introduced into the ATCC31833 strain by electroporation according to the method of Rest et al. [Appl. Microbiol. Biotech., 52, 541 (1999)] to select kanamycin-resistant strains. The structure of the chromosome obtained from one of the selected kanamycin-resistant strains was analyzed by Southern hybridization [Molecular Cloning: A Laboratory Manual, 3rd Ed., 2001, Cold Spring Harbor Laboratory Press]. It was confirmed that pCΔptsH was integrated into the chromosome by Campbell-type homologous recombination.

The above transformant (the primary recombinant) was spread on Suc agar medium (100 g of sucrose, 7 g of meat extract, 10 g of peptone, 3 g of sodium chloride, 5 g of yeast extract (Difco Laboratories Inc.) and 18 g of Bacto Agar (Difco Laboratories Inc.) in 1 liter of water, and adjusted to pH 7.2) and cultured at 30° C. for one day to select colonies for growing. A strain carrying the sacB gene cannot grow on this medium owing to the conversion of sucrose into a suicide substrate [J. Bacteriol., 174, 5462 (1991)]. In contrast, a strain lacking the sacB gene due to the second homologous recombination that took place between the wild-type ptsH gene and the mutant ptsH gene existing close to each other on the chromosome can grow on this medium because no suicide substrate is formed. At the second homologous recombination, either the wild-type ptsH gene or the mutant ptsH gene is deleted together with sacB gene. Deletion of the wild-type gene together with sacB gene results in a gene replacement of the wild-type gene with the mutant gene.

The chromosomal DNA of the secondary recombinant was prepared according to the method of Saito et al. [Biochim. Biophys. Acta, 72, 619 (1963)]. The nucleotide sequence of the ptsH gene region amplified by PCR was determined according to a usual method. As a result, it was found that the secondary recombinant ptsH, which was termed "ΔptsH strain" is the desired ptsH-disrupted strain lacking a 216-bp fragment in the structural gene.

The ΔptsH strain and its parent strain, ATCC31833 strain, were individually spread on a MM agar medium, which was a minimal medium containing glucose as the sole carbon source (10 g of glucose, 0.4 g of magnesium sulfate heptahydrate, 4 g of ammonium chloride, 2 g of urea, 3 g of dibasic potassium phosphate, 1 g of potassium dihydrogen phosphate, 10 mg of iron sulfate heptahydrate, 1 mg of manganese sulfate pentahydrate, 5 mg of nicotinic acid, 0.1 mg of biotin, 5 mg of thiamine hydrochloride, and 20 g of Bacto Agar in 1 liter of water, and adjusted to pH 7.2; hereinafter referred to as "glucose medium"), and cultured at 30° C. for 2 days. The ATCC 31833 strain grew well, whereas the ΔptsH strain did not grow.

In contrast, when using a medium containing ribose, which is a non-PTS sugar, in place of glucose that was contained in the glucose medium (hereinafter referred to as "ribose medium"), both the ΔptsH strain and ATCC31833 strain grew well. Table 1 shows the results.

It was concluded from the results that the ΔptsH strain is a ptsH-deficient strain (hereinafter referred to as "ptsH-disrupted strain").

(4) Acquisition of a ptsH-Disrupted Strain with Restored Growth on the Glucose Medium (Hereinafter Referred to as "Suppressor Mutant")

The ΔptsH strain was spread on BY agar medium (containing 7 g of meat extract, 10 g of peptone, 3 g of sodium chloride, 5 g of yeast extract, and 15 g of Bacto Agar in 1 L of water, and adjusted to pH 7.2), and cultured at 30° C. for 18 hours.

The cells of the strain that grew on the BY agar medium were suspended in physiological saline to $10^8$ cells/ml concentration. The suspension was spread onto the MM agar medium and cultured at 30° C. for 6 days. As a result, colonies grew on the MM agar medium at a frequency of about $10^{-5}$. These colonies were spread on the MM agar medium and cultured at 30° C. for 2 days, using the ΔptsH strain and the ATCC31833 strain as controls. The ΔptsH strain did not grow on the MM agar medium. In contrast, all of the obtained colonies grew almost as well as colonies of the ATCC31833 strain on the MM ager medium.

One of the suppressor mutant strains was isolated to obtain a SupH strain. The *Corynebacterium glutamicum* SupH strain was deposited in accordance with the Budapest Treaty under the accession number of FERM BP-10998 on Aug. 22, 2008, at the independent administrative agency, National Institute of Advanced Industrial Science and Technology, International Patent Organism Depositary (Central 6, 1-1, Higashi 1-Chome, Tsukuba-shi, Ibaraki-ken, 305-8566, Japan).

Table 1 shows the growth of the ATCC31833 strain, ΔptsH strain and SupH strain, each of which was spread on the glucose medium and the ribose medium, and cultured at 30° C. for 2 days.

Further, the ATCC31833 strain, the ΔptsH strain and the SupH strain were spread on the glucose medium and the ribose medium described above in (3) and on the ribose medium to which a glucose analogue, 2-deoxyglucose, had been added to a concentration of 1 mg/ml. These strains were cultured at 30° C. for 2 days to examine their growth. Table 1 shows the results.

TABLE 1

| | | Ribose medium 2-deoxyglucose | |
| --- | --- | --- | --- |
| Strain | Glucose medium | Not added | Added |
| ATCC31833 | + | + | − |
| ΔptsH | − | + | + |
| SupH | + | + | + |

+: The strain grew.
−: The strain did not grow.

As shown in Table 1, the wild-type strain did not grow in the presence of 1 mg/ml 2-deoxyglucose, whereas the ΔptsH strain and the SupH strain grew. It was concluded from the results that the SupH strain became capable of taking glucose into cells via a non-PTS system.

(5) Growth of the SupH Strain in the Glucose Medium

Figure 2:
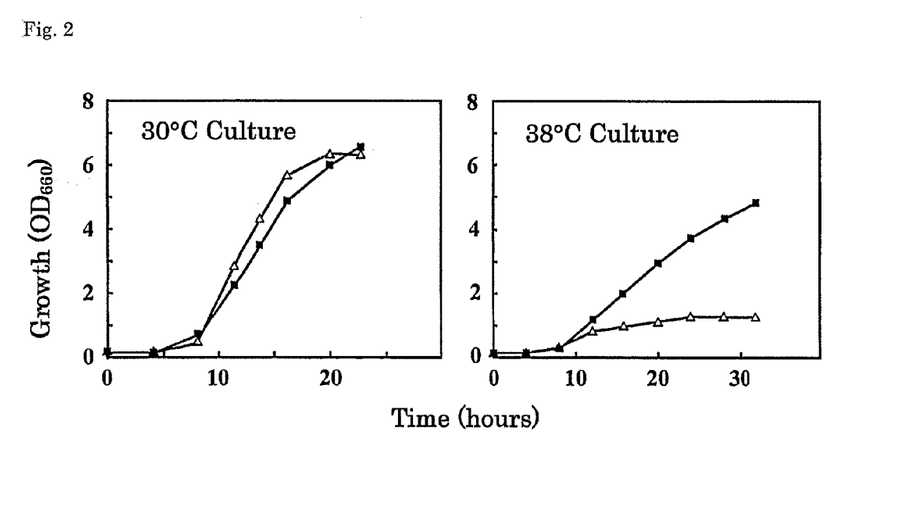
FIG. 2 shows graphs of the growth of the SupH strain and the ATCC31833 strain in glucose media.

The SupH strain and the ATCC31833 strain were spread on the BY agar medium, and cultured at 30° C. for 18 hours. Cells of each of the strains that grew on the medium were inoculated into a large test tube containing 5 ml of the BY medium (same composition as the BY agar medium except for not containing agar), and cultured at 30° C. for 12 hours. 0.05 mL of each resulted culture was inoculated into two L-type test tubes containing 5 ml of MM medium (same composition as the MM agar medium except for not containing agar). One of each pair of the test tubes was cultured at 30° C. under aerobic conditions, and the other of each pair of the test tubes was cultured under aerobic conditions at 38° C. FIG. 2 shows the growth measured at OD660.

As shown in FIG. 2, both the SupH strain and the ATCC31833 strain grew well at 30° C. In contrast, the growth of the ATCC31833 strain at 38° C., i.e., under high-temperature conditions was markedly lowered and the growth almost stopped during the culture, whereas the SupH strain grew well at 38° C.

The results thus show that the SupH strain exhibits an excellent high-temperature resistance in liquid culture in the glucose medium, compared to the ATCC31833 strain.

EXAMPLE 2

Production of L-Lysine Using the SupH Strain lysC311 mutation was introduced into the SupH strain obtained in Example 1, according to the disclosure of Japanese Unexamined Patent Publication No. 2002-191370 (U.S. Pat. No. 7,332,310), to prepare a SupH (lysC311) strain.

One platinum loop amount of cells of the SupH(lysC311) strain cultured on the BY agar medium at 30° C. for 24 hours was inoculated into a large test tube containing 5 ml of seed medium (20 g of glucose, 7 g of meat extract, 10 g of peptone, 3 g of sodium chloride, and 5 g of yeast extract in 1 L of water, and adjusted to pH 7.2, after which 10 g of calcium carbonate was added), and cultured at 30° C. for 15 hours. 0.5 ml of this seed culture solution was inoculated into a large test tube containing 5 ml of main culture medium (50 g of glucose, 10 g of corn steep liquor, 45 g of ammonium sulfate, 2 g of urea, 0.5 g of potassium dihydrogen phosphate, 0.5 g of magnesium sulfate heptahydrate, and 0.3 mg of biotin in 1 liter of water, and adjusted to pH 7.0, after which 30 g of calcium carbonate was added), and cultured on a shaker at 30° C. to 37° C. for 72 hours. After the cells were removed from the culture by centrifugation, the amount of L-lysine monohydrochloride accumulated in the supernatant was determined by high-performance liquid chromatography (HPLC) to confirm that L-lysine was produced.

EXAMPLE 3

Production Test of L-lysine using the SupH Strain

It is known that a L-lysine producing strain can be obtained by introducing lysC311 mutation (Thr311→Ile) into a *Corynebacterium glutamicum* wild-type strain (Japanese Unexamined Patent Publication No. 2002-191370, Appl. Microbiol. Biotechnol., 58, 217 (2002)). The method of introducing this mutation is also described in detail in Japanese unexamined patent publication (Japanese Unexamined Patent Publication No. 2002-191370). Based on such information, lysC311 mutation was introduced into the SupH strain obtained in Example 1 and its parent strain, ATCC31833 strain. The ATCC31833 strain and the SupH strain each containing lysC311 mutation were designated ATCC31833 (lysC311) strain and SupH (lysC311) strain, respectively.

Production test of L-lysine using the ATCC31833 strain (lysC311) and the SupH (lysC311) strain thus obtained was conducted by culturing those strains using a test tube in the following manner. One platinum loop amount of the cells of each strain that was cultured at 30° C. in the BY agar medium for 24 hours was inoculated into a large test tube containing 5 ml of seed medium (20 g of glucose, 7 g of meat extract, 10 g of peptone, 3 g of sodium chloride, and 5 g of yeast extract in 1 liter of water, adjusted to pH 7.2, after which 10 g of calcium carbonate was added), and cultured at 30° C. for 13 hours. 0.5 ml of this seed culture was inoculated into a large test tube containing 5 ml of main culture medium (50 g of glucose, 10 g of corn steep liquor, 45 g of ammonium sulfate, 2 g of urea, 0.5 g of potassium dihydrogen phosphate, 0.5 g of magnesium sulfate heptahydrate, and 0.3 mg of biotin in 1 liter of water, adjusted to pH 7.0, after which 30 g of calcium carbonate was added), and cultured on a shaker at 33° C. for 72 hours. After the cells were removed from each culture by centrifugation, the amount of L-lysine hydrochloride accumulated in the supernatant was determined by high-performance liquid chromatography (HPLC). Table 2 shows the results.

TABLE 2

| Strain | Growth (OD$_{660}$) | L-lysine hydrochloride (g/l) |
|---|---|---|
| ATCC31833 (lysC311) | 12 | 2.4 |
| SupH (lysC311) | 12 | 3.6 |

As is clear from Table 2, the SupH (lysC311) strain prepared by introducing lysC311 mutation into the suppressor mutant strain of the present invention produced L-lysine hydrochloride in a significantly increased amount, as compared to the ATCC31833 (lysC311) strain prepared by introducing lysC311 mutation into the ATCC31833 strain.

EXAMPLE 4

Production Test of L-Lysine Using Cgl0181 or Cgl3058 Gene-Expressing Strain

A plasmid containing DNA fragment comprising the nucleotide sequence shown in SEQ ID NO: 13 and a plasmid containing DNA fragment comprising the nucleotide sequence shown in SEQ ID NO: 15 were prepared in the following manner.

The DNA comprising the nucleotide sequence shown in SEQ ID NO: 13 encodes the amino acid sequence of Cgl0181 (NCgl0178) shown in SEQ ID NO: 12. The DNA comprising the nucleotide sequence shown in SEQ ID NO: 15 encodes the amino acid sequence of Cgl3058 (NCgl2953) shown in SEQ ID NO: 14.

(1) Construction of a DNA Fragment for Expressing Cgl0181 or Cgl3058

PCR was performed using two pairs of primers, i.e., DNAs comprising the nucleotide sequences shown in SEQ ID NOS: 5 and 6, and DNAs comprising the nucleotide sequences shown in SEQ ID NOS: 8 and 9, and using the chromosomal DNA of the ATCC31833 strain as a template. The amplified DNA fragments of about 1 kb and about 1.88 kb were mixed. Using this mixture as a template and using DNA fragments comprising the nucleotide sequences shown in SEQ ID NOS: 5 and 9 as a primer set, second PCR was performed. As a result, the DNA fragment for expressing Cgl0181 (an approximate 2.88 kb DNA fragment wherein DNA encoding Cgl0181 was inserted downstream of the gapA promoter) was obtained.

Similarly, PCR was performed using two pairs of primers, i.e., DNA fragments comprising the nucleotide sequences shown in SEQ ID NOS: 5 and 7, and DNA fragments comprising the nucleotide sequences shown in SEQ ID NOS: 10 and 11, and using the chromosomal DNA of the ATCC31833 strain as a template. The amplified DNA fragments of about 1 kb and about 1.68 kb were mixed. Using this mixture as a template, second PCR was performed. As a result, DNA fragment for expressing Cgl3058 (an approximate 2.68 kb DNA fragment wherein DNA encoding Cgl3058 was inserted downstream of a gapA promoter) was obtained.

(2) Construction of a Plasmid Containing DNA Fragment for Expressing Cgl0181 or Cgl3058

A plasmid pCS299P [Appl. Microbiol. Biotech., 63, 592 (2004)], and DNA fragment for expressing Cgl0181 obtained above in (1) were cleaved with restriction enzymes, SalI and XhoI, and then ligase reaction was performed using DNA Ligation Kit Ver. 1 (produced by Takara Shuzo Co., Ltd.). The Plasmid pCS299P and the DNA fragment for expressing Cgl3058 obtained above in (1) were cleaved with restriction enzyme, BamHI, and then ligase reaction was performed in a similar manner. Using the reaction products, *Escherichia coli* DH5a was transformed according to a usual method.

The obtained strain was cultured on LB agar medium containing 20 mg/ml kanamycin to select a transformant. The transformant was inoculated into LB medium containing 20 mg/ml kanamycin, and cultured overnight. Plasmids were prepared from the culture by the alkaline SDS method. The nucleotide sequences of the obtained plasmids were analyzed. It was confirmed that the one plasmid had a structure such that an approximate 2.88 kb DNA fragment was inserted into pCS299P, and another plasmid had a structure such that about 2.68 kb DNA fragment was inserted into pCS299P. These plasmids were designated pPgapA-0181 and pPgapA-3058, respectively.

(3) Growth Characteristic Test Using the ΔptsH Strain Containing pPgapA-0181 or pPgapA-3058 pPgapA-0181 and pPgapA-3058 were individually introduced into ΔptsH strains as obtained in Example 1 to prepare a ΔptsH/pPgapA-0181 strain and a ΔptsH/pPgapA-3058 strain, respectively. Each of these strains was spread on the glucose medium, the ribose medium, and the medium prepared by adding 2-deoxyglucose to the ribose medium at a concentration of 1 mg/ml, and cultured at 30° C. for 2 days to examine their growth. Table 3 shows the results.

TABLE 3

| Strain | Glucose medium | Ribose medium 2-deoxyglucose | |
|---|---|---|---|
| | | Not added | Added |
| ΔptsH | − | + | + |
| ΔptsH/pPgapA-0181 | + | + | + |
| ΔptsH/pPgapA-3058 | + | + | + |

As shown in Table 3, the ΔptsH strain was not able to grow on the glucose medium, whereas the ΔptsH/pPgapA-0181 strain and the ΔptsH/pPgapA-3058 strain grew. Furthermore, both the ΔptsH/pPgapA-0181 strain and ΔptsH/pPgapA-3058 strain also grew even in the presence of 2-deoxyglucose similarly to the ΔptsH strain. The above results revealed that both the ΔptsH/pPgapA-0181 strain and the ΔptsH/pPgapA-3058 strain are capable of taking glucose into cells via a non-PTS system.

(4) Production Test of L-lysine Using the ATCC31833 (lysC311) Strain Containing pPgapA-0181 or pPgapA-3058 pPgapA-0181 and pPgapA-3058 were individually introduced into L-lysine-producing ATCC31833 (lysC311) strains as obtained in Example 3 to produce an ATCC31833 (lysC311)/pPgapA-0181 strain and an ATCC31833 (lysC311)/pPgapA-3058 strain, respectively. A production test of L-lysine was performed using these strains in a manner similar to the test tube culture described in Example 3. After the cells were removed from the culture by centrifugation, the amount of L-lysine hydrochloride accumulated in the supernatant was determined by high-performance liquid chromatography (HPLC). Table 4 shows the results.

TABLE 4

| Strain | Growth ($OD_{660}$) | L-lysine hydrochloride (g/l) |
|---|---|---|
| ATCC31833 (lysC311) | 12 | 2.4 |
| ATCC31833 (lysC311)/ΔptsH/pPgapA-0181 | 13 | 3.2 |
| ATCC31833 (lysC311)/ΔptsH/pPgapA-3058 | 13 | 3.4 |

As is clear from Table 4, both of the ATCC31833 (lysC311) strain containing pPgapA-0181 and the ATCC31833 (lysC311) strain containing pPgapA-3058 produced L-lysine hydrochloride in a significantly increased amount, as compared to the ATCC31833 (lysC311) strain not containing any of the plasmids, pPgapA-0181 and pPgapA-3058.

INDUSTRIAL APPLICABILITY

According to the present invention, a process for efficiently producing a useful substance can be provided.

SEQUENCE LISTING FREE TEXT

SEQ ID NO: 1—Description of Artificial Sequence: Synthetic DNA

SEQ ID NO: 2—Description of Artificial Sequence: Synthetic DNA

SEQ ID NO: 3—Description of Artificial Sequence: Synthetic DNA

SEQ ID NO: 4—Description of Artificial Sequence: Synthetic DNA

SEQ ID NO: 5—Description of Artificial Sequence: Synthetic DNA

SEQ ID NO: 6—Description of Artificial Sequence: Synthetic DNA

SEQ ID NO: 7—Description of Artificial Sequence: Synthetic DNA

SEQ ID NO: 8—Description of Artificial Sequence: Synthetic DNA

SEQ ID NO: 9—Description of Artificial Sequence: Synthetic DNA

SEQ ID NO: 10—Description of Artificial Sequence: Synthetic DNA

SEQ ID NO: 11—Description of Artificial Sequence: Synthetic DNA

The invention claimed is:

1. A process for producing an amino acid, comprising culturing a microorganism in a medium; forming and accumulating the amino acid in a culture; and collecting the amino acid from the culture, wherein the microorganism (a) belongs to coryneform bacteria, (b) has an ability to produce the amino acid, and (c) has an enhanced ability to transport a sugar selected from the group consisting of glucose, fructose, and sucrose into a cell via a protein defined in any one of [1] to [4] below by introducing a recombinant DNA encoding the protein into a coryneform bacterium that is used as a host;

[1] a protein comprising the amino acid sequence of SEQ ID NO: 14;

[2] a protein consisting of an amino acid sequence of SEQ ID NO: 14, wherein 1 to 20 amino acid residues are added, deleted, or substituted, wherein the protein has myo-inositol transport activity, and wherein the protein is homologous to a protein consisting of SEQ ID NO: 14;

[3] a protein encoded b DNA comprising the nucleotide sequence of SEQ ID NO: 15; and

[4] a protein encoded by DNA comprising a nucleotide sequence having 95% or more identity to the nucleotide sequence shown in SEQ ID NO: 15, wherein the protein has myo-inositol transport activity, and wherein the protein is homologous to a protein consisting of SEQ ID NO: 14.

2. The process according to claim 1, wherein the microorganism belonging to coryneform bacteria is selected from the group consisting of the genera *Corynebacterium*, *Brevibacterium* and *Microbacterium*.

3. The process according to claim 1, wherein the microorganism belonging to coryneform bacteria is the genus *Corynebacterium*.

4. The process according to claim 1, wherein the microorganism belonging to coryneform bacteria is *Corynebacterium glutamicum*.

5. The process according to claim 1, wherein the microorganism is *Corynebacterium glutamicum* SupH (FERM BP-10998).

6. The process according to claim 1, wherein the culturing is performed at 35° C. to 38° C.

7. The process according to claim 1, wherein the amino acid is lysine.

* * * * *